United States Patent [19]
Piel et al.

[11] Patent Number: 5,991,037
[45] Date of Patent: Nov. 23, 1999

[54] HIGH SPATIAL RESOLUTION ELLIPSOMETRY DEVICE

[75] Inventors: Jean-Philippe Piel, Marly le Roi; Jean-Louis Stehle, Colombes; Dorian Zahorski, Vanves, all of France

[73] Assignee: Societe de Production et de Recherches Appliquees, France

[21] Appl. No.: 09/000,386

[22] PCT Filed: Jul. 3, 1996

[86] PCT No.: PCT/FR96/01035

§ 371 Date: Jan. 27, 1998

§ 102(e) Date: Jan. 27, 1998

[87] PCT Pub. No.: WO97/07392

PCT Pub. Date: Feb. 27, 1997

[30] Foreign Application Priority Data

Aug. 11, 1995 [FI] Finland .................................. 95/09779

[51] Int. Cl.[6] .................................................. G01N 21/21
[52] U.S. Cl. ........................................................ 356/369
[58] Field of Search ................................ 359/209, 557; 356/369

[56] References Cited

U.S. PATENT DOCUMENTS 5,329,357  7/1994  Bernoux et al. .
5,742,426  4/1998  York ........................................ 359/209

FOREIGN PATENT DOCUMENTS 2602338  5/1988  France .
2595471  6/1988  France .

OTHER PUBLICATIONS

"Spatially Resolved Ellipsometry"; Journal of Applied Physics, Aug. 1, 1986, vol. 60, No. 3; pp. 859–873, Erman M. et al.

"Magneto–Optical Ellipsometer"; Review of Scientific Instruments, May 1985, pp. 687–690; Nederpel, P.Q.J. et al.

"Presentation of a New Spectroscopic Phase Modulated Ellipsmeter for In–Situ–and Ex–Situ–Applications"; Laser und Optoelektronik; Apr. 24 (1992), No. 2, pp. 63–67; Brings R.

*Primary Examiner*—Robert H. Kim
*Assistant Examiner*—Zandra Smith
*Attorney, Agent, or Firm*—Christie, Parker & Hale, LLP

[57] ABSTRACT

The ellipsometry device includes a first focusing device, combined with a first optical system, for focusing the light beam from the first optical system onto the sample, a second focusing device, combined with a second optical system, for focusing the beam reflected by the sample surface onto the input of the second optical system, and an optical correction device for correcting, together with the first and second focusing devices, the position of the focused reflected beam so as to reject the interference reflections generated by the surface of the sample opposite the light beam receiving surface, and to obtain a maximum signal level at the photodetector.

18 Claims, 1 Drawing Sheet

HIGH SPATIAL RESOLUTION ELLIPSOMETRY DEVICE

BACKGROUND OF THE INVENTION

The invention relates to the field of ellipsometry, and more particularly to spectroscopic ellipsometry.

It finds a general application in any field in which ellipsometry is used, and more particularly in micro-electronics in the optical inspection of a laser surface treatment, such as the annealing of amorphous silicon samples by excimer laser. It thus finds a very particular application in the manufacture of liquid crystal screens consisting of at least one layer of amorphous silicon deposited on a transparent substrate. It also finds an application notably in surface cleaning, polishing and preparation.

In the patent FR-A-2602338 and in the article: JOURNAL OF APPLIED PHYSICS, Aug. 1, 1986, US, vol. 60, No. 3, ISSN 0021-8979, pages 859–873, XP00579985, M. ERMAN et al, "Spatially resolved ellipsometry"; an ellipsometer comprises in general terms a light source, a sample holder, a photodetector, a first optical system mounted between the light source and the sample holder, and a second optical system mounted between the sample holder and the photodetector. The first optical system illuminates the sample supported by the sample holder, at an oblique angle of incidence, by means of a polarized light beam. The second optical system collects the light sent back by the sample. In practice, first focusing means, associated with the first optical system, focus the illumination beam coming from the said first optical system on the sample whilst second focusing means, associated with the second optical system, focus the beam reflected by the surface of the sample on the entrance of the second optical system.

In the patent application entitled "Device and method for laser surface treatment", filed by the Applicant under the number 95 09778 and published under the number FR-A2737806 (for all useful purposes, the content of this application forms an integral part of the present application), a characterization of a sample by ellipsometry is advantageously used in the manufacture of liquid crystal screens, in order to optimize the process of recrystallization of the silicon by laser by controlling the application of the laser energy by means of the ellipsometry measurement.

In such a manufacture of liquid crystal screens, the sample holder supports a sample comprising at least one layer of a material of the amorphous silicon type, of given thickness and deposited on a transparent substrate (for example glass) of given thickness. The front face of the sample receives here the illumination radiation whilst the rear face of the sample is in contact with the sample holder.

Because of the thickness of the transparent substrate, the interface between the rear face of the said sample and the sample holder reflects towards the second optical system and the photodetector an interference light beam which may falsify the ellipsometry measurements.

SUMMARY OF THE INVENTION

The present invention affords precisely a solution to this problem.

It relates to an ellipsometry device of the type described above which is characterized by the fact that the second focusing means receive the radiation reflected by the front face of the sample and focus it on the entrance pupil of the photodetector, whilst the interference reflections generated by the rear face of the sample in contact with the sample holder are routed out of the entrance pupil of the photodetector, and by the fact that the ellipsometer also comprises optical correction means disposed between the analyzer and the entrance pupil of the photodetector and suitable for being controlled in order to finely adjust the position of the useful reflected radiation focused by the second focusing means on the entrance pupil of the photodetector.

Thus, in the manufacture of liquid crystal screens where the layer of silicon to be treated rests on a transparent substrate, such a device has the advantage of improving the quality of the measurement by rejecting the interference reflections and finely adjusting the position of the useful reflected beam on the entrance pupil of the photodetector. It should be noted that, in the state of the art mentioned above, the treatment of the samples does not come up against the problem resolved according to the invention since the layer of the sample to be treated does not rest on a transparent substrate.

Other characteristics and advantages of the invention will emerge in the light of the following detailed description and the drawings in which the single figure depicts schematically an improved ellipsometer according to the invention.

DETAILED DESCRIPTION OF THE INVENTION

Figure 1:
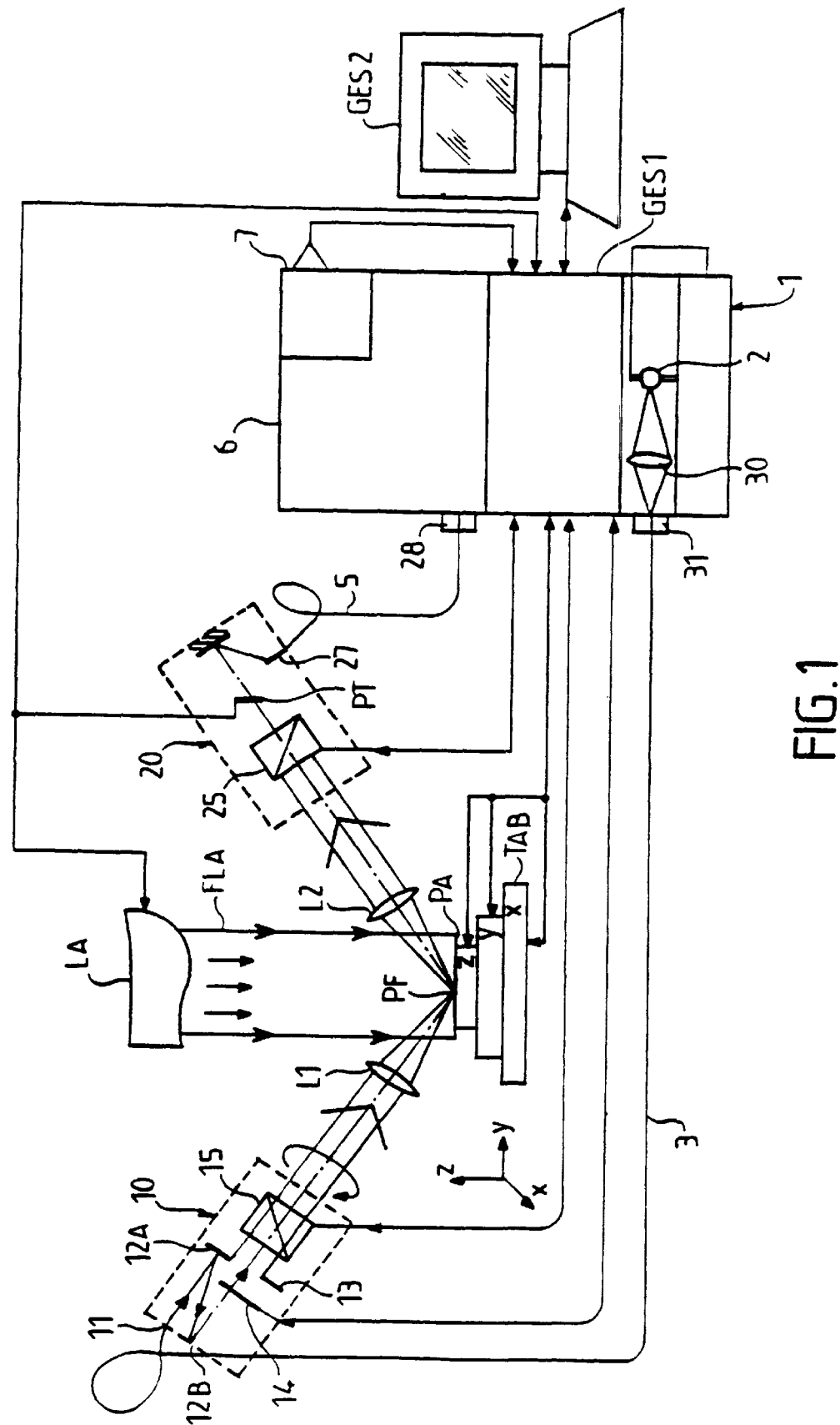
FIG. 1 illustrates spectroscopic ellipsometer of the present invention.

On the single figure (FIG. 1.), the reference EL designates a spectroscopic ellipsometer, for example the one sold by the Applicant under the sales reference ES4G. An improvement of such an ellipsometer is described in the French patent No 86 03188 (FR-A-2 595 471).

A power supply 1 excites a wide-band light source 2, such as a high-pressure xenon arc lamp. A first optical system 10, including a polarizer 15, transforms the light beam coming from the source 2 into a beam which strikes a panel PA mounted on a panel-support table TAB, preferably able to move in three orthogonal directions X, Y and Z.

The useful light is that reflected by the panel PA, in such a way that it can be considered to be symmetrical with the incident beam with respect to a perpendicular to the surface of the panel PA.

This reflected light is taken up by a second optical system 20 comprising an analyzer 25, so as to be applied to the entry slot of a prism monochromator 6 able to be tuned in the optical band of the light source. The light coming from the monochromator 6 is applied to a photodetector 7 comprising an array of photo diodes, for example of 512 or 1024 pixels, enabling the wavelength detection to be carried out.

An electronic control unit GES1 acts:
- on the polarizer 15, in order to control its influence on the state of polarisation of the incident light beam, for example in the case of a rotating polarizer, its continued setting in rotation,
- on the stepping motors associated with the table TAB, in order to control their movement in terms of X-Y-Z,
- on the robot ROB in order to control the extraction of a panel from the storage rack in which the said panels to be treated are stored, the movement of the panel thus extracted towards the panel-support table and the positioning of the panel on the table at a chosen location, as well as the gripping of the panel after treatment and the placing thereof in the initial storage rack or another storage rack, on the obturator 14, in order to control its operation, on the analyzer 25, in order to control its orientation through a stepping motor, on the monochromator 6, in order to define its tuning wavelength, on the laser source LA, in order to control its flux.

The signal coming from the photodetector 7 is applied to the management means GES1, so as to be recorded in connection with the rotation of the polarizer 15, and other collected data including notably the position of the panel to be treated, that of the analyzer and the wavelength to which each measurement corresponds.

This information, optionally pre-processed by the electronic unit GES1, is transmitted to processing means GES2 such as a microcomputer. According to coordinates taken on the panel (associated with the position struck on each occasion by the spot), the processing means derive the ellipsometry information (for example "psi tangent" and "delta cosine"), and then curves representing the surface state and/or the multilayer structure of the panel to be treated.

A chassis, preferably a single one, comprises the power supply 1 to the xenon lamp 2, the management means GES1, the monochromator 6, the detector 7 and if applicable the processing means GES2.

In practice, the light radiation from the source 2 is transmitted by a lens 30 to an entry coupler 31 of an optical fiber 3. The latter joins the optical system 10, which comprises a fiber exit coupler 11, two return mirrors 12A and 12B, a collimation diaphragm 13, an obturator 14 and the polarizer 15.

According to the invention, the parallel beam coming from the polarizer 15 is focused by a convergent lens L1 onto a focal point PF of the panel to be treated, which gives an "ellipsometry spot". The lens L1 is disposed at the level of the object plane of the panel.

Symmetrically, the reflected radiation is focused by another convergent lens L2 onto the analyzer 25. The lens L2 is disposed at the level of the image plane of the panel. The lenses L1 and L2 are optically combined. They improve the spatial resolution of the ellipsometer, as will be described in more detail below.

The light beam coming from the analyzer 25 is focused by a mirror 26 onto the entry sensor 27 of a second optical fiber 5.

The light coming from the exit coupler 28 of the optical fiber 5 is taken up by a lens in order to be applied to the entry slot of the monochromator 6.

In the case of a panel designed to produce TFT transistors (thin film transistors), this panel comprises a layer of amorphous silicon to a depth of around 50 nm resting on a glass substrate with a thickness of around 0.7 to 1.2 mm. It has been observed that the interface between the rear face of the glass substrate and its support (panel-support table) generates an interference reflected light beam which can falsify the ellipsometry measurements. This phenomenon exists in many other applications.

According to the invention, the optical assembly formed by the lenses L1 and L2 enables this interference reflection to be eliminated.

This is because the diameter of the spot coming from the convergent lens L1 onto the surface of the panel is for example around 100 $\mu$m. This size is much less than the average thickness of the glass substrates normally used. The useful part of the light reflected by the sample (that is to say that relating to the different interfaces between the layers in the laser annealing application) remains correctly taken up by the convergent lens L2, so as to be taken or refocused onto the optical fiber 5. On the other hand, the spatial position of the light spot due to the reflection on the front face of the sample being different from that of the light spot due to the reflection on the rear face of the sample, the latter is not (or is appreciably less) returned by the lens L2 to the optical fiber 5, which makes it possible to eliminate it (or almost so).

It is in the event unexpected for the use of lenses such as L1 and L2 to produce a focusing on the beam conventionally applied to the sample to resolve the problem posed; this is because ellipsometry, a technique which is already tricky, becomes even more so if it is desired to work at high resolution; and a priori difficulties are expected in altering the said conventional beams.

In the example of an application to the annealing of large panels, it should be remarked that the positioning of the panels on the sample holder TAB in the Z direction is a critical operation which must be controlled perfectly with a view to preserving the high spatial resolution of the ellipsometry device.

According to the invention, this operation is controlled as follows.

Firstly, the curvature of each type of panel in the vertical direction Z is taken into account by adjusting the ellipsometry spot with respect to Z. The value of the adjustment is stored according to coordinates taken on the panel (optionally by zones on the panel). The cartography of the profile of each type of panel is stored in memory in the computer GES2.

Secondly, in the method of controlling the laser surface treatment, the position of impact of the analysis light spot on a chosen area of a panel, thus recorded and stored to memory, is re-used for the series of panels to be processed.

However, this is not always sufficient since differences in deformations can arise between different panels of the same type.

According to the invention, a fine adjustment of the position of the spot (the light beam reflected by the sample and focused by the lenses L1 and L2) on the exit fiber 5 is obtained by inclining, with respect to the optical beam, a transparent plate PT (a parallel-face sheet) disposed between the analyzer 25 and the entry coupler of the optical fiber 5. The rotation axis or axes are tangent to the surface of the sheet. This rotation is controlled by the management means GES1 so as always to be at the maximum signal level on the array of the photodetector 7.

We claim:

1. An ellipsometry device comprising: a light source; a sample holder; a photodetector; a first optical system mounted between the light source and the sample holder, and having first polarization optical means in order to illuminate a sample at an oblique angle of incidence, by means of a polarized light beam; a second optical system mounted between the sample holder and the photodetector, and having second polarization optical means for collecting a light returned by the sample; first focusing means associated with the first optical system and able to focus an illumination beam coming from said first optical system onto the sample; and second focusing means associated with the second optical system and able to focus a beam reflected by the surface of the sample onto an entrance of the second optical system wherein the sample holder supports a sample, which comprises at least one layer of a chosen material, of given thickness, and whose front face is able to receive an illumination radiation, said layer being deposited on a transparent substrate of given thickness whose rear face is in contact with the sample holder, the second focusing means to receive a radiation reflected by the front face of the layer of the sample and focus it on an entrance pupil of the photodetector, whilst interference reflections generated by the rear face of the substrate of the sample in contact with the sample holder are routed out of the entrance pupil of the photodetector, the second polarization optical means include an analyzer, and the ellipsometry device further comprises optical correction means disposed between the analyzer and the entrance pupil of the photodetector and able to be controlled in order to finely adjust a position of the reflected radiation focused by the second focusing means on the entrance pupil of the photodetector.

2. The ellipsometry device of claim 1 wherein the optical correction means comprise a transparent sheet able to be inclined with respect to a useful reflected optical beam focused by the second focusing means in order to adjust a position of said useful reflected beam so as to be at a maximum signal level at the photodetector.

3. The ellipsometry device of claim 1 wherein the ellipsometry device is spectroscopic.

4. The ellipsometry device of claim 1 wherein the first focusing means comprise a convergent lens disposed downstream of the first optical system.

5. The elliosometry device of claim 1 wherein the second focusing means comprise a convergent lens disposed upstream of the second optical system.

6. The ellipsometry device of claim 1, wherein the first polarization optical means include a polarizer, and the first optical system further comprises a first optical fiber disposed between the light source and the polarizer.

7. The ellipsometry device of claim 1, wherein the second optical system further comprises a second optical fiber, disposed between the analyzer and the photodetector, the second optical fiber having an entrance coupler and an exit coupler which delivers a radiation to the photodetector, where the entrance coupler of the second optical fiber is the entrance pupil of the photodetector.

8. The elliosometry device of claim 1 wherein the sample holder is able to move in three directions orthogonal to each other.

9. The ellipsometry device for inspecting a sample, the sample including at least one layer of a first given thickness of a chosen material deposited on a transparent substrate of a second given thickness and having a front face and a rear face, comprising:
    a light source;
    a sample holder for supporting the sample;
    a photodetector;
    a first optical system, mounted between the light source and the sample holder, having a first polarization optical means for illuminating the sample when the sample is placed on the sample holder, at an oblique angle of incidence, using a polarized light beam;
    a second optical system, mounted between the sample holder and the photodetector, having a second polarization optical means for collecting a reflected light beam from the sample when the sample is placed on the sample holder, an entrance pupil for the photodetector and an optical correction device disposed between the second polarization optical means and the entrance pupil;
    a first focusing device focusing the polarized light beam onto the sample when the sample is placed on the sample holder; and
    a second focusing device focusing the reflected light beam onto an entrance of the second optical system,
    wherein, when the sample is placed on the sample holder, the front face of the sample is able to receive the polarized light beam, and the rear face of the sample is in contact with the sample holder, and the second focusing device is able to receive the reflected light beam from the front face of the sample and focus it on the entrance pupil through the second polarization optical means while interference reflections generated by the rear face of the sample are routed out of the entrance pupil, and the optical correction device is controllable in order to finely adjust a position of the reflected light beam focused by the second focusing device.

10. The ellipsometry device of claim 9 wherein the optical correction device comprises a transparent plate, which is inclinable with respect to the reflected light beam focused by the second focusing device, for adjusting a position of the reflected light beam to have a maximum signal level at the photodetector.

11. The ellipsometry device of claim 9 wherein the ellipsometry device is spectroscopic.

12. The ellipsometry device of claim 9 wherein the first focusing device comprises a first convergent lens disposed between the first optical system and a focal point.

13. The ellipsometry device of claim 9 wherein the second focusing device comprises a second convergent lens disposed between the second optical system and a focal point.

14. The ellipsometry device of claim 9, wherein the first optical system further comprises a first optical fiber disposed between the light source and the first polarization optical means.

15. The ellipsometry device of claim 9 wherein the second optical system further comprises a second optical fiber, disposed between the second polarization optical means and the photodetector, the second optical fiber having an entrance coupler and an exit coupler for delivering a radiation to the photodetector, where the entrance coupler of the second optical fiber is the entrance pupil of the photodetector.

16. The ellipsometry device of claim 9, wherein the sample holder can be controlled to move in three directions, orthogonal to each other.

17. A method of using an ellipsometry device, comprising:
    providing a sample having at least one layer of a chosen material of given thickness, and whose front face is able to receive an illumination radiation, said layer deposited on a front face of a transparent substrate of given thickness;
    placing the sample on a sample holder so that a rear face of the transparent substrate is in contact with the sample holder;
    illuminating the sample at an oblique angle of incidence with a polarized light beam using a first optical system having first polarization optical means and mounted between a light source and the sample holder, focusing the polarized light beam onto the sample using first focusing means;
    receiving a reflected light from the sample with a second optical system having second polarization optical means for collecting the reflected light from the sample, said second optical system mounted between the sample holder and a photodetector, focusing the reflected light onto an entrance of the second optical system using second focusing means where the second focusing means focus the reflected light on an entrance pupil of the photodetector, while interference reflections generated by the rear face of the substrate are routed out of the entrance pupil; and
    finely adjusting a position of the reflected light on the entrance pupil by controlling optical correction means disposed between the second polarization optical means and the entrance pupil.

18. A method of using an ellipsometry device of claim 17, further comprising the step of:
    moving the sample holder in three orthogonal directions.

* * * * *